United States Patent [19]
King et al.

[11] Patent Number: 6,127,379
[45] Date of Patent: Oct. 3, 2000

[54] BENZOPYRAN, BENZOTHIOPYRAN AND BENZOFURAN DERIVATIVES AS 5-HT4 ANTAGONISTS

[75] Inventors: Francis David King; Laramie Mary Gaster, both of Bishop's Stortford; Graham Francis Joiner, Brentwood, all of United Kingdom

[73] Assignee: SmithKline Beecham p.l.c., Brentford, United Kingdom

[21] Appl. No.: 08/284,448

[22] PCT Filed: Feb. 1, 1993

[86] PCT No.: PCT/GB93/00214

§ 371 Date: Aug. 3, 1994

§ 102(e) Date: Aug. 3, 1994

[87] PCT Pub. No.: WO93/16072

PCT Pub. Date: Aug. 19, 1993

[51] Int. Cl.$^7$ .......................... A01N 43/42; A01N 43/40; C07D 221/02; C07D 211/06
[52] U.S. Cl. .......................... 514/299; 514/310; 514/320; 514/329; 546/112; 546/143; 546/195; 546/202
[58] Field of Search ........................... 546/195, 202, 546/143, 112; 514/320, 329, 310, 299

[56] References Cited

U.S. PATENT DOCUMENTS

| | | | |
|---|---|---|---|
| 4,859,683 | 8/1989 | Youssetyeh et al. | 549/112 |
| 5,374,637 | 12/1994 | Van Daele et al. | 514/320 |

FOREIGN PATENT DOCUMENTS

| | | |
|---|---|---|
| 0 231 139 | 8/1987 | European Pat. Off. . |
| 0 234 872 | 8/1987 | European Pat. Off. . |
| WO93/03725 | 3/1993 | WIPO . |
| WO93/05040 | 3/1993 | WIPO . |

OTHER PUBLICATIONS

Thominet et al, Chemical Abstract vol. 89 No. 6329, "Pham. sub. 2,3–(alkylene dioxy) benzamides" (1978).

Van Daele et al, Chemical Abstract, vol. 114 No. 164012, "Prep. N–(3–methoxy–4–piperidinyl) . . . endocrin gastrointestinal motility" 1990.

Primary Examiner—Alan L. Rotman
Assistant Examiner—Raymond Covington
Attorney, Agent, or Firm—Soma G. Simon; William T. King; Charles M. Kinzig

[57] ABSTRACT

Compounds of the general formula (I), and pharmaceutically acceptable salts thereof,

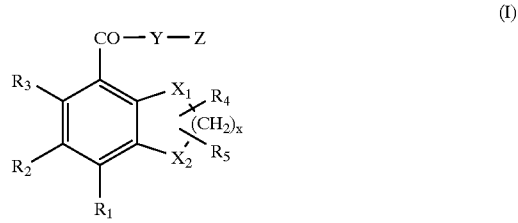

(I)

in which $X_1$—$(CH_2)_x$—$X_2$ and the aromatic carbon atoms to which they are attached form a 5–7 membered ring, wherein:

one of $X_1$ and $X_2$ is O, S or $CH_2$ and the other is $CH_2$;
x is 1, 2 or 3;
$R_1$ is hydrogen, amino, halo, $C_{1-6}$ alkyl, hydroxy or $C_{1-6}$ alkoxy;
$R_2$ is hydrogen, halo, $C_{1-6}$ alkyl, $C_{1-6}$ alkoxy, nitro, amino or $C_{1-6}$ alkylthio;
$R_3$ is hydrogen, halo, $C_{1-6}$ alkyl, $C_{1-6}$ alkoxy or amino;
$R_4$ and $R_5$ are independently hydrogen or $C_{1-6}$ alkyl;
Y is O or NH;
Z is of sub-formula (a), (b) or (c):

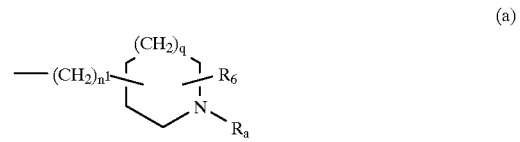

(a)

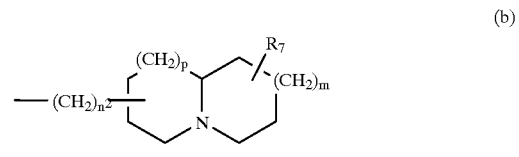

(b)

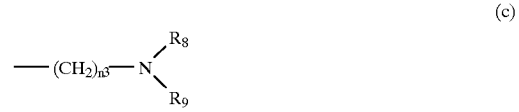

(c)

wherein
$n^1$ is 1, 2, 3 or 4; $n^2$ is 1 or 2; $n^3$ is 2, 3, 4 or 5;
q is 0, 1, 2 or 3; p is 0, 0 or 2; m is 0, 1 or 2;
$R_a$ is hydrogen or a lipophilic group, such as $C_{1-12}$ alkyl or aralkyl; or
$R_a$ is $(CH_2)_r$—$R_{10}$ wherein r is 2 or 3 and $R_{10}$ is selected from cyano, hydroxyl, $C_{1-6}$ alkoxy, phenoxy, $C(O)C_{1-6}$ alkyl, $COC_6H_5$, —$CR_{11}R_{12}$, $NR_{11}COR_{12}$, $SO_2NR_{11}R_{12}$ or $NR_{11}SO_2R_{12}$ wherein $R_{11}$ and $R_{12}$ are hydrogen or $C_{1-6}$ alkyl; and
$R_6$, $R_7$ and $R_8$ are independently hydrogen or $C_{1-6}$ alkyl; and
$R_9$ is hydrogen or $C_{1-10}$ alkyl;
and compounds of formula (I) wherein the CO-Y linkage is replaced by a heterocyclic bioisostere, are disclosed to have 5-HT4 antagonist activity.

11 Claims, No Drawings

BENZOPYRAN, BENZOTHIOPYRAN AND BENZOFURAN DERIVATIVES AS 5-HT4 ANTAGONISTS The present application is based on PCT application number WO 93/16072, filed Feb. 1, 1993, which is based on the following priority applications: Great Britain application number 9202510.5, filed Feb. 6, 1992, Great Britain application number 9215499.6, filed Jul. 21, 1992, Great Britain application number 9221446.9, filed Oct. 13, 1992 and Great Britain application number 9225788.0, filed Dec. 10, 1992.

This invention relates to the use of compounds as 5-$HT_4$ receptor antagonists in the treatment of gastrointestinal disorders, CNS disorders including migraine and/or cardiovascular disorders, and to certain novel compounds having 5-$HT_4$ receptor antagonist activity.

European Journal of Pharmacology 146 (1988), 187–188, and Naunyn-Schmiedeberg's Arch. Pharmacol. (1989) 340:403–410, describe a non classical 5-hydroxytryptamine receptor, now designated the 5-$HT_4$ receptor, and that ICS 205-930, which is also a 5-$HT_3$ receptor antagonist, acts as an antagonist at this receptor.

WO 91/16045 (SmithKline and French Laboratories Limited) describes the use of cardiac 5-$HT_4$ receptor antagonists in the treatment of atrial arrhythmias and stroke.

EP-A-501322 (Glaxo Group Limited) describes indole derivatives having 5-$HT_4$ antagonist activity.

Some 5-$HT_3$ receptor antagonists have been disclosed as of potential use in the treatment of certain aspects of irritable bowel syndrome [EP-A-189002 (Sandoz Limited) and EP-A-201165 (Beecham Group p.l.c)].

5-$HT_3$ receptor interactions which are of potential use in the treatment of IBS are those associated either with the visceral pain and abnormal perception of sensation aspects of this disease, or they are related to the ability of some 5-$HT_3$ receptor antagonists to cause constipation in volunteers.

Some 5-$HT_3$ receptor antagonists have been disclosed as of potential use in the treatment of gastrointestinal disorders associated with upper gut motility [EP-A-226266 (Glaxo Group Ltd.) and EP-A-189002 (Sandoz Limited)]. 5-$HT_3$ receptor antagonists are also well known antiemetics, such as ondansetron, granisetron and tropisetron [Drugs of the Future 1989, 14 (9) p.875 —F. D. King and G. J. Sanger].

EP-A-234872 (Adria), US 4859683 (Rorer) and EP-A-307172 (Lilly) describe 5-$HT_3$ receptor antagonists derived from a benzoic acid nucleus, 2,3-disubstituted by alkyleneoxy.

It has now been discovered that certain of the compounds embraced by the general formulae disclosed therein, and related compounds, have 5-$HT_4$ receptor antagonist properties, and are therefore of potential use in the treatment of IBS or atrial arrhythmias and stroke.

The compounds of the present invention also have a potential use in the treatment of CNS disorders such as anxiety and/or migraine, in the treatment of upper gut motility disorders and as antiemetics.

Accordingly, the present invention provides the use of a compound of formula (I) or a pharmaceutically acceptable salt thereof:

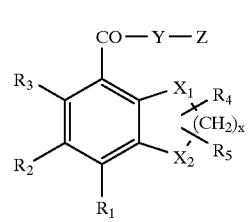

in which $X_1$—$(CH_2)_x$—$X_2$ and the aromatic carbon atoms to which they are attached form a 5–7 membered ring wherein:

one of $X_1$ and $X_2$ is O, S or $CH_2$ and the other is $CH_2$;

x is 1, 2 or 3;

$R_1$ is hydrogen, amino, halo, $C_{1-6}$ alkyl, hydroxy or $C_{1-6}$ alkoxy;

$R_2$ is hydrogen, halo, $C_{1-6}$ alkyl, $C_{1-6}$ alkoxy, nitro, amino or $C_{1-6}$ alkylthio;

$R_3$ is hydrogen, halo, $C_{1-6}$ alkyl, $C_{1-6}$ alkoxy or amino;

$R_4$ and $R_5$ are independently hydrogen or $C_{1-6}$ alkyl;

Y is O or NH;

Z is of sub-formula (a), (b) or (c):

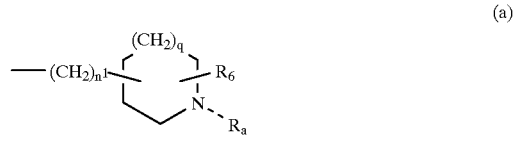

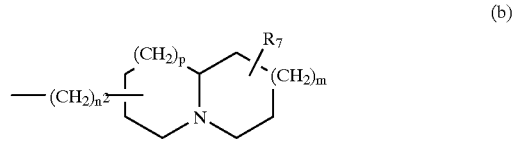

wherein $n^1$ is 1, 2, 3 or 4; $n^2$ is 1 or 2; $n^3$ is 2, 3, 4 or 5;

q is 0, 1, 2 or 3; p is 0, 1 or 2; m is 0, 1 or 2;

$R_a$ is hydrogen or a lipophilic group, such as $C_{1-12}$ alkyl or aralkyl; or $R_a$ is $(CH_2)_rR_{10}$ wherein r is 2 or 3 and $R_{10}$ is selected from cyano, hydroxyl, $C_{1-6}$ alkoxy, phenoxy, $C(O)C_{1-6}$ alkyl, $COC_6H_5$, —$CR_{11}R_{12}$, $NR_{11}COR_{12}$, $SO_2NR_{11}R_{12}$ or $NR_{11}SO_2R_{12}$ wherein $R_{11}$ and $R_{12}$ are hydrogen or $C_{1-6}$ alkyl; and $R_6$, $R_7$ and $R_8$ are independently hydrogen or $C_{1-6}$ alkyl; and $R_9$ is hydrogen or $C_{1-10}$ alkyl;

or a compound of formula (I) wherein the CO-Y linkage is replaced by a heterocyclic bioisostere;

in the manufacture of a medicament for use as a 5-$HT_4$ receptor antagonist.

Examples of alkyl or alkyl containing groups include $C_1$, $C_2$, $C_3$, $C_4$, $C_5$, $C_6$, $C_7$, $C_8$, $C_9$, $C_{10}$, $C_{11}$ or $C_{12}$ branched, straight chained or cyclic alkyl, as appropriate. $C_{1-4}$ alkyl groups include methyl, ethyl n- and iso-propyl, n-, iso-, sec and tert-butyl. Cyclic alkyl includes cyclopropyl, cyclobutyl, cyclopentyl, cyclohexyl, cycloheptyl and cyclooctyl.

Aryl includes phenyl and naphthyl optionally substituted by one or more substituents selected from halo, $C_{1-6}$ alkyl and $C_{1-6}$ alkoxy.

Halo includes fluoro, chloro, bromo and iodo,.

A suitable bioisostere for the amide or ester linkage containing Y in formula (I), is of formula (d)

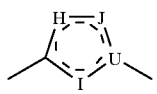

(d)

wherein
the dotted circle represents one or two double bonds in any position in the 5-membered ring; H, J and I independently represent oxygen, sulphur, nitrogen or carbon, provided that at least one of H, J and I is other than carbon; U represents nitrogen or carbon.

Suitable examples of (d) are as described for X, Y and Z in EP-A-328200 (Merck Sharp & Dohme Ltd.), such as an oxadiazole moiety.

Suitable examples of the $X_1$—$(CH_2)_x$—$X_2$ include O—$(CH_2)_2$—$CH_2$, O—$(CH_2)_3$—$CH_2$, O—$CH_2$—$CH_2$, or corresponding values wherein $X_1$=$X_2$=$CH_2$, wherein any of the methylene linkages are optionally mono- or di-substituted by $C_{1-6}$ alkyl groups, such as methyl. Preferably $X_1$—$(CH_2)_2$—$X_2$ is O—$(CH_2)_2$—$CH_2$.

$R_1$ is preferably hydrogen or amino.

$R_2$ is preferably hydrogen or halo.

$R_3$ is preferably hydrogen or halo.

$R_4$ and $R_5$ are often hydrogen. When $R_4$/$R_5$ is $C_{1-6}$ alkyl, it is often methyl. In particular $R_4$ and $R_5$ are methyl such that the disubstituent containing $X_1$ and $X_2$ is $X_1$—$C(CH_3)_2$—$X_2$.

Y is preferably O or NH.

When Z is of sub-formula (a), $n^1$ is preferably 2, 3 or 4 when the azacycle is attached at the nitrogen atom and $n^1$ is preferably 1 when the azacycle is attached at a carbon atom, such as the 4-position when q is 2.

When Z is of sub-formula (b), $n^2$ is preferably such that the number of carbon atoms between the ester or amide linkage is from 2 to 4 carbon atoms.

Suitable values for p and m include p=m=1; p=0, m=1; p=1, m=2.

When Z is of sub-formula (c), $n^3$ is preferably 2, 3 or 4.

$R_8$ and $R_9$ are preferably both alkyl, especially one of $R_8$ and $R_9$ is $C_4$ or larger alkyl.

Specific values of Z of particular interest are as follows:

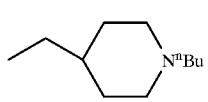

(i)

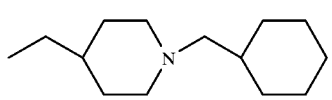

(ii)

-continued

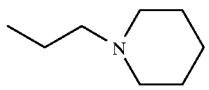

(iii)

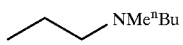

(iv)

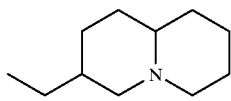

(v)

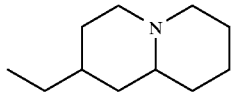

(vi)

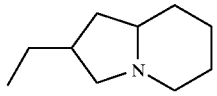

(vii)

The invention also provides novel compounds within formula (I) with side chains (i), (ii), (iii), (iv), (v), (vi) or (vii). In a further aspect, the piperidine ring in (i), (ii) or (iii) may be replaced by pyrrolidinyl or azetidinyl, and/or the N-substituent in (i) or (ii) may be replaced by $C_3$ or larger alkyl or optionally substituted benzyl.

In an alternative aspect, the N-substituent in formula (i) or (ii) may be replaced by $(CH_2)_nR^4$, as defined in formula(I) and in relation to the specific examples of EP-A-501322.

The invention also provides novel compounds within formula (I) having $X_1$—$(CH_2)_x$—$X_2$ as O—$(CH_2)_2$—$CH_2$, in particular those wherein the side chain Z is of sub-formula (a) or (c).

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

Examples of pharmaceutically acceptable salts include quaternary derivatives of the compounds of formula (I) such as the compounds quaternised by compounds $R_x$-T wherein $R_x$ is $C_{1-6}$ alkyl, phenyl-$C_{1-6}$ alkyl or $C_{5-7}$ cycloalkyl, and T is a radical corresponding to an anion of an acid. Suitable examples of $R_x$ include methyl, ethyl and n- and iso-propyl; and benzyl and phenethyl. Suitable examples of T include halide such as chloride, bromide and iodide.

Examples of pharmaceutically acceptable salts also include internal salts such as N-oxides.

The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is herein referred to.

It will also be realised that the $(CH_2)_n2$ moiety in compounds of formula (I) wherein Z is (b), may adopt an α or β or configuration with respect to the fused azabicyclic moiety.

The compounds of formula (I) wherein CO—Y is an ester or amide linkage are prepared by conventional coupling of the Z moiety with the appropriate acid. Suitable methods are as described in GB 21 25398A (Sandoz Limited), GB 1593146A, EP-A-36269 and EP-A-289170 (Beecham Group p.l.c.). When CO—Y is replaced by a heterocyclic bioisostere, suitable methods are described in EP-A-328200 (Merck Sharp & Dohme Limited). Reference is also made to EP-A-501322 (Glaxo Group Limited).

Aza(bi)cyclic side chain intermediates are known compounds or may be prepared according to the methods described in PCT/GB92/01519 and /01612 (SmithKline Beecham p.l.c.).

The compounds of the present invention are $5\text{-HT}_4$ receptor antagonists and it is thus believed may generally be used in the treatment or prophylaxis of gastrointestinal disorders, cardiovascular disorders and CNS disorders.

They are of potential interest in the treatment of irritable bowel syndrome (IBS), in particular the diarrhoea aspects of IBS, i.e., these compounds block the ability of 5-HT to stimulate gut motility via activation of enteric neurones. In animal models of IBS, this can be conveniently measured as a reduction of the rate of defaecation. They are also of potential use in the treatment of urinary incontinence which is often associated with IBS.

They may also be of potential use in other gastrointestinal disorders, such as those associated with upper gut motility, and as antiemetics. In particular, they are of potential use in the treatment of the nausea and gastric symptoms of gastrooesophageal reflux disease and dyspepsia. Antiemetic activity is determined in known animal models of cytotoxic agent induced emesis.

Specific cardiac $5\text{-HT}_4$ receptor antagonists which prevent atrial fibrillation and other atrial arrhythmias associated with 5-HT, would also be expected to reduce occurrence of stroke (see A. J. Kaumann 1990, Naumyn-Schmiedeberg's Arch. Pharmacol. 342, 619–622, for appropriate animal test method).

Anxiolytic activity is likely to be effected via the hippocampus (Dumais et al 1988, Mol Pharmacol., 34, 880–887). Activity can be demonstrated in standard animal models, the social interaction test and the X-maze test.

Migraine sufferers often undergo situations of anxiety and emotional stress that precede the appearance of headache (Sachs, 1985, Migraine, Pan Books, London). It has also been observed that during and within 48 hours of a migraine attack, cyclic AMP levels are considerably increased in the cerebrospinal fluid (Welch et al, 1976, Headache 16, 160–167). It is believed that a migraine, including the prodomal phase and the associated increased levels of cyclic AMP are related to stimulation of $5\text{-HT}_4$ receptors, and hence that administration of a $5\text{-HT}_4$ antagonist is of potential benefit in relieving a migraine attack.

The invention also provides a pharmaceutical composition comprising a compound of formula (I), or a pharmaceutically acceptable salt thereof, and a pharmaceutically acceptable carrier.

Such compositions are prepared by admixture and are usually adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared try dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of irritable bowel syndrome, dyspepsia, atrial arrhythmias and stroke, anxiety and/or migraine in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contain 0.05 to 1000 mg for example 0.5 to 500 mg, of the compound of the invention. Unit doses may be administered once or more than once a day, for example, 2, 3 or 4 times a day, more usually 1 to 3 times a day, that is in the range of approximately 0.0001 to 50 mg/kg/day, more usually 0.0002 to 25 mg/kg/day.

No adverse toxicological effects are indicated within the aforementioned dosage ranges.

The invention also provides a compound of formula (I) or a pharmaceutically acceptable salt thereof for use as an active therapeutic substance, in particular for use in the treatment of irritable bowel syndrome, gastro-oesophageal reflux disease, dyspepsia, atrial arrhythmias and stroke, anxiety and/or migraine.

The following Examples illustrate the preparation of compounds of formula (I); the following descriptions relate to intermediates.

A preferred compound corresponds to any example, but wherein there is an amino substituent in the 4-position and a chloro substituent in the 5-position of the benzoic acid nucleus depicted in formula (I).

| | | | Examples | | |
|---|---|---|---|---|---|
| | R1 | R2 | R3 | $X_1/X_2$ | Y | Z |
| E1 | H | H | H | O—$(CH_2)_2$—$CH_2$ | O | (i) |
| E2 | H | H | H | O—$CH_2$—$CH_2$ | O | (i) |
| E3 | H | Cl | H | O—$(CH_2)_2$—$CH_2$ | O | (i) |
| E4 | H | H | H | O—$CH(CH_3)_2$—$(CH_2)_2$ | O | (i) |
| E5 | H | Cl | H | O—$CH(CH_3)_2$—$CH_2$ | O | (i) |
| E6 | $NH_2$ | Cl | H | O—$(CH_2)_2$—$CH_2$ | O | (i) |
| E7 | H | Cl | H | O—$(CH_2)_2$—$CH_2$ | O | (iii) |
| E8 | H | Cl | H | O—$(CH_2)_2$—$CH_2$ | NH | (i) |
| E9 | H | Cl | H | O—$CH(CH_3)_2$—$(CH_2)_2$ | O | (i) |
| E10 | H | H | H | S—$(CH_2)_2$—$CH_2$ | O | (i) |
| E11 | H | Br | H | S—$(CH_2)_2$—$CH_2$ | O | (i) |
| E12 | $NH_2$ | Cl | H | O—$(CH_2)_2$—$CH_2$ | NH | (i) |

EXAMPLE 1

(1-Butyl-4-piperidyl)methyl-[2H]-3,4-dihydro-1-benzopyran-8-carboxylate (E1)

To a stirred solution of [2H]-3,4-dihydro-1-benzopyran-8-carboxylic acid (0.3 g) in dichloromethane (15 ml) at 0° C. under nitrogen, was added oxalyl chloride (0.16 ml) and dry dimethylformamide (3 m drops). After 1 hour, the solvents were evaporated under reduced pressure. The residual acid chloride was dissolved in dry THF (20 ml) and added dropwise to a solution of the lithium anion of 1-butyl-4-piperidinemethanol in dry THF, prepared by treating a solution of 1-butyl-4-piperidinemethanol (0.29 g) in dry THF (20 ml) with butyllithium (1.1 ml of a 1.6 molar solution in hexane), at 0° C. under nitrogen for 15 minutes. After stirring at ambient temperature overnight, the reaction mixture was diluted with water, the volatile solvent was evaporated under reduced pressure, and the product was extracted into dichloromethane. The organic phase was dried ($Na_2SO_4$) and the solvent was evaporated under reduced pressure. The residue was chromatographed through a short flash silica column using an increasing proportion of methanol in chloroform (1%, 2%). The product was isolated as the hydrochloride salt from IPA/$Et_2O$ to give the title compound (177 mg).

mp 166–8° C. $^1$H NMR 250 MHz ($CDCl_3$) (free base) δ:7.62(d,1H), 7.19(d,1H), 6.85(t,1H), 4.30(t,2H), 4.15(d, 2H), 3.02(d,2H), 2.83(t,2H), 2.45–2.25(m,2H), 2.1–1.9(m, 4H), 1.9–1.65(m,3H), 1.6–1.2(m,6H), 0.92(t,3H)

EXAMPLE 2

(1-Butyl-4-piperidyl)methyl-2,3-dihydrobenzofuran-7-carboxylate hydrochloride (E2)

To a stirred solution of 2,3-dihydrobenzofuran-7-carboxylic acid (D1) (0.2 g) in dichloromethane (15 ml) at 0° C. under nitrogen was added oxalyl chloride (0.12 ml) and dry dimethylformamide (3 drops). After 1 hour the solvents were evaporated under reduced pressure. The residual acid chloride was dissolved in dichloromethane (15 ml) and treated with a solution of 1-butyl-4-piperidine methanol (0.21 g) in dichloromethane (10 ml) and triethylamine (0.19 ml). After stirring at ambient temperature overnight, the reaction mixture was washed with saturated $NaHCO_3$ and the organic phase was dried ($Na_2SO_4$). The solvent was evaporated under reduced pressure and the residue chromatographed through a short flash silica column, eluting with increasing proportions of methanol in chloroform (1%, 2%). The product was isolated as the hydrochloride salt from IPA/$Et_2O$ to give the title compound (84 mg).

mp 187–9° C. $^1$H NMR 250 MHz ($CDCl_3$) (free base) δ:7.72(d,1H), 7.35(d,1H), 6.88(t,1H), 4.72(t,2H), 4.19(d, 2H), 3.22(t,2H), 3.1–2.9(d,2H), 2.5–2.25(m,2H), 2.1–1.2(m, 11H), 0.92(t,3H)

EXAMPLE 3

(1-Butyl-4-piperidyl)methyl-6-chloro-[2H]-3,4-dihydro-1-benzopyran-8-carboxylate (E3)

Following the procedure outlined in Example 1 (except that methyllithium was used in a place of n-butyllithium), 6-chloro-[2H]-3,4-dihydro-1-benzopyran-8-carboxylic acid (300 mg) was converted to the title compound (143 mg, 28%).

$^1$H NMR 250 MHz ($CDCl_3$) δ:7.55 (s, 1H), 7.15 (s, 1H), 4.29 (t, 2H), 4.15 (d, 2H), 3.05 (brd, 2H), 2.80 (t, 2H), 2.5–2.25 (m, 2H), 2.18–1.10 (m, 13H), 0.94 (t, 3H)

EXAMPLE 4

2,2-Dimethyl-[2H]-3,4-dihydro-1-benzopyran-8-(1-butyl-4-piperidyl)methylcarboxylate hydrochloride (E4)

To a solution of 2,2-dimethyl-[2H]-3,4-dihydro-1-benzopyran-8-carboxylic acid (EP-A-307172) (300 mg) in acetonitrile (20 ml) was added N, N'-carbonyidiimidazole (236 mg). Stirring was continued at ambient temperature for 1 h. The solvent was concentrated in vacuo to afford crude imidazolide.

Methyllithium (1.5M in diethyl ether, 0.97 ml) was added dropwise to a cooled (0° C.) solution of 1-butyl-4-piperidinemethanol (250 mg) in dry THF (10 ml) under a nitrogen atmosphere. Stirring was continued at room temperature for 10 min. A solution of the imidazolide in dry THF (10 ml) was added and stirring continued overnight. Water was added and the solvent concentrated in vacuo. The residue was partitioned between chloroform and water. The organic phase was dried ($Na_2SO_4$), filtered and concentrated. The residue was chromatographed on silica using chloroform and ethanol as eluant to afford pure ester (471 mg) as an oil. Treatment with ethereal HCl and trituration of the resultant gum with diethyl ether gave title compound as a solid.

$^1$H NMR 250 MHz ($CDCl_3$) δ:7.60(d,1H), 7.19(d,1H), 6.82(t,1H), 3.99(d,2H), 2.93–3.03(m,2H), 2.81 (t,2H), 2.28–2.37(m,2H), 1.61–2.02(m,7H), 1.23–1.56(m,12H inc s,6H), 0.94(t,3H)

EXAMPLE 5

7-(1-Butyl-4-piperidyl)methyl-5-chloro-2,3-dihydro-2,2-dimethyl-benzofurancarboxylate (E5)

Following the procedure outlined in Example 4, 5-chloro-2,3-dihydro-2,2-dimethylbenzofuran-7-carboxylic acid was converted to the title compound.

mp 225–6° C. (hydrochloride salt) $^1$H NMR 250 MHz (CDCl$_3$) (free base) δ:7.65(d,1H), 7.22 (d,1H), 4.12(d,2H), 2.92–3.11 (m,4H incl. s2H), 2.28–2.38 (m,2H), 1.22–2.0 (m, 17H inc s,6H), 0.92 (t,3H)

EXAMPLE 6

(1-Butyl-4-piperidyl)methyl-5-amino-6-chloro-[2H]-3,4-dihydro-1-benzopyran-8-carboxylate hydrochloride (E6)

Following the procedure outlined in Example 4, 5-amino-6-chloro-[2H]-3,4-dihydro-1-benzopyran-8-carboxylic acid (D4) (200 mg) was converted to the title compound (68 mg 19%).

mp 209–213° C. $^1$H NMR 250 MHz (CDCl$_3$) (free base) δ:7.7(s,1H), 4.39(brs, 2H), 4.22(t,2H), 4.1 0(d,2H), 3.05 (brd,2H), 2.6–2.25(m,4H), 2.2–1.93(m,4H), 1.9–1.68(m, 3H), 1.65–1.2(m,6H), 0.92(t,3H)

EXAMPLE 7

(1-Piperidyl)ethyl-6-chloro-[2H]-3,4-dihydro-1-benzopyran-8-carboxylate hydrochloride (E7)

Following the procedure outlined in Example 1, except that MeLi was used in place of butyllithium, 6-chloro-[2H]-3,4-dihydro-1-benzopyran-8-carboxylic acid (390 mg) was converted to the title compound (182 mg, 28%) mp 185–7° C.

$^1$H NMR 250 MHz (CDCl$_3$) (free base) δ:7.58(s,1H), 7.1 5(s,1H), 4.4(t,2H), 4.29(t,2H), 2.88–2.65(m,4H), 2.6–2.35 (m,4H), 2.15–1.9(m,2H), 1.7–1.3(m,6H)

EXAMPLE 8

(1-Butyl-4-piperidyl)methyl-6-chloro-[2H]-3,4-dihydro-1-benzopyran-8-carboxamide hydrochloride (E8)

A solution of 6-chloro-[2H]-3,4-dihydro-1-benzopyran-8-carboxylic acid (200 mg) in dry dichloromethane (6 ml) was treated with oxalyl chloride (0.13 ml) and dry dimethylformamide (2 drops) under nitrogen. After stirring for four hours at ambient temperature the solvent was evaporated under reduced pressure. The resulting acid chloride was dissolved in dry dichloromethane (6 ml) and added to a stirring solution of 1-butylpiperidin-4-ylmethylamine (160 mg) in dry dichloromethane (5 ml) containing triethylamine (0.14 ml). After stirring at ambient temperature overnight under nitrogen, the reaction mixture was washed with NaHCO$_3$ and the organic phase dried over Na$_2$SO$_4$. The solvent was evaporated under reduced pressure to give the product which was purified using column chromatography (SiO$_2$, methanol/chloroform), and converted to the hydrochloride salt (E61) (138 mg, 37%) mp 227–9° C.

$^1$H NMR 250 MHz (CDCl$_3$) (free base) δ:7.98(s,1H), 7.12(s,1H), 4.35(t,2H), 3.35(t,2H), 3.08(brd, 2H), 2.85(t, 2H), 2.5–2.3(m,2H), 2.2–1.92(m,4H), 1.9–1.2(m,9H), 0.92 (t,3H)

EXAMPLE 9

6-Chloro-2,2-dimethyl-[2H]-3,4-dihydro-1-benzopyran-8-(1-butyl-4-piperidyl)methyl carboxylate hydrochloride (E9)

Following the procedure outlined in Example 4, 6-chloro-2,2-dimethyl-[2H]-3,4-dihydro-1-benzopyran-8-carboxylic acid (D5) (1 g) was converted to the title compound (310 mg)

$^1$H NMR 250 MHz (CDCl$_3$) (free base) δ:7.55(d,1H), 7.16(d,1H), 4.13(d,2H), 2.98(bd, 2H), 2.79(t,2H), 2.32(t, 2H), 1.68–2.00(m,7H), 1.24–1.54(m,12H inc s,6H), 0.92(t, 3H)

EXAMPLE 10

(1-Butyl-4-piperidyl)methylthiochroman-8-carboxylate (E10)

This was prepared according to the general method described in Example 1. Thus thiochroman-8-carboxylic acid (0.160 g, 0.825 mmol) (D6) was converted to the title compound (0.145 g, 53%) which was subsequently transformed into its hydrochloride salt m.pt 157–158° C.

$^1$H NMR (250 MHz, CDCl$_3$) (free base), δ:7.82 (d, 1H), 7.17 (d, 1H), 7.00 (t, 1H), 4.15 (d, 2H), 3.00 (m, 4H), 2.87 (t, 2H), 2.38 (t, 2H), 2.20–1.95 (m, 5H), 1.80 (m, 2H), 1.50 (m, 4H), 1.30 (m, 2H), 0.90 (t, 3H).

EXAMPLE 11

(1-Butyl-4-piperididyl)methyl-6-bromothiochroman-8-carboxylate (E11)

This was prepared according to the general method described in Example 1. Thus 6-bromothiochroman-8-carboxylic acid (0.318 g, 1.17 mmol) (D7) was converted to the title compound (0.217 g, 44%) which was subsequently transformed into its hydrochloride salt. m.pt. 197–1980.

$^1$H NMR (200 MHz, CDCl$_3$) (free base) δ:7.90 (d, 1H), 7.30 (d, 1H), 4.20 (d, 2H), 3.00 (m, 4H), 2.88 (t, 2H), 2.32 (t, 2H), 2.10 (m, 2H), 2.00–1.70 (m, 4H), 1.55–1.20 (m, 7H), 0.92 (t, 3H).

EXAMPLE 12

5-Amino-(1-butyl-4-piperidyl)methyl-6-chloro-[2H]-3,4-dihydro-1-benzopyran-8-carboxamide (E12)

A solution of 5-amino-6-chloro-[2H]-3,4-dihydro-1-benzopyran-8-carboxylic acid (D4, 200 mg ) in acetonitrile (6 ml) was treated with bis-carbonyldiimidazole (171 mg) and the resulting solution was stirred at room temperature for 2 hours. A solution of (1-butyl-4-piperidyl) methylamine (150 mg) in acetonitrile (10 ml) was added and the reaction mixture was stirred at room temperature for 15 hours. The solvent was removed in vacuo and the residue partitioned between water and dichloromethane. The dichloromethane layer was removed and the aqueous extracted further with dichloromethane. The organic extracts were combined and washed with water, then dried (Na$_2$SO$_4$) and concentrated to give a yellow gum that was purified by column chromatography on silica using CHCl$_3$ with increasing quantities of MeOH as eluant to give the title compound ats an off white solid, 30 mg mp 65–6° C.

$^1$H NMR (250 MHz CDCl$_3$) δ:8.0 (s,1H), 7.96–7.8 (m,1H), 4.45–4.15 (m,4H,) 3.32 (t,2H), 3.02 (d,2H), 2.53 (t, 2H), 2.39 (t,2H), 2.2–1.9 (m,4H), 1.86–1.15(m,9H), 0.92 (t,3H)

DESCRIPTIONS

Description 1 (intermediate for Example 2)
[2H]-3,4-Dihydro-1-benzopyran-8-carboxylic acid Following the procedure outlined in EP-A-3071 72 Example 15, [2H]-3,4-dihydro-1-benzopyran (0.85 g) was converted to the title compound (D1) (0.77 g)

$^1$H NMR (200 MHz)(CDCl$_3$) δ:8.0(d,1H), 7.3(d, 1H), 7.0(t,1H), 4.45(t,2H), 2.89(t,2H), 2.25–2.0(m,2H)

Description 2 (intermediate for Example 2)
2,3-Dihydrobenzofuran-7-carboxylic acid Following the procedure outlined in EP-A-307172, Example 15, 2,3-dihydrobenzofuran (0.59 g) was converted to the title compound (D2) (0.41 g)

$^1$H NMR 250 MHz (CDCl$_3$) δ:7.82(d,1H), 7.44(d,1H), 6.96(t,1H), 4.80(t,2H), 3.30(t,2H)

Description 3 (intermediate for Example 3)
6-Chloro-[2H],4-dihydro-1-benzopyran-8-carboxylic acid A solution of [2H]-3,4-dihydro-1-benzopyran-8-carboxylic acid (D1) (150 mg) in glacial acetic acid (10 ml) was treated with a solution of 1.3 equivalents of chlorine (80 mg) in glacial acetic acid (2.8 mls) dropwise with ice-cooling. After stirring overnight at ambient temperature the solvents were evaporated under reduced pressure, and the residue triturated with diethyl ether to give the title compound (D3) (64 mg, 36%).

$^1$H NMR 200 MHz (CDCl$_3$) δ:10.78 (brs, 1H), 7.95 (s, 1H), 7.25 (s, 1H), 4.45 (t, 2H), 2.88 (t, 2H), 2.25–2.0 (m, 2H)

Description 4 (intermediate for Example 6)
a) Methyl(4-acetylamino-2-propargyloxy)benzoate A solution of methyl-4-acetylamino-2-hydroxybenzoate (prepared as described in EP-A-234872) (5 g) in a mixture of dry tetrahydrofuran (100 ml) and dry dimethylformamide (150 ml) was treated with 1 equivalent of sodium hydride (0.72 g of an 80% dispersion in oil). After stirring for 1 hour under nitrogen, 2.5 equivalents of propargylbromide (5.33 ml) were added, and the mixture was heated under reflux for three days. The solvents were evaporated under reduced pressure and the residue partitioned between 10% sodium hydroxide and ethyl acetate. The organic phase was dried over Na$_2$SO$_4$ and evaporated under reduced pressure to give a red oil which, after trituration with 60°–80° petrol-ether gave the title compound as a light tan powder (4.95 g, 84%)

$^1$H NMR 200 MHz (CDCl$_3$) δ:7.91 (brs, 1H), 7.81 (d,1H), 7.68(s, 1H), 7.05(d, 1H), 4.78(d,2H), 3.86(s,3H), 2.54(m, 1H), 2.2(s,3H)

b) Methyl(5-acetamido-[2H]-1-benzopyran)-8-carboxylate

A solution of methyl(4-acetamido-2-propargyloxy) benzoate (6.38 g) in 1,2-dichlorobenzene (65 ml) was heated under reflux under nitrogen for 60 hours. The solvent was evaporated under reduced pressure and the residue purified on a silica column, eluting with methanol/chloroform, to give the title compound as a tan solid (3.47 g, 54%)

$^1$H NMR 200 MHz (CDCl$_3$) δ:7.79(brs,1H), 7.64(d,1H), 7.3(d,1H), 6.46(d,1H), 5.85(m,1H), 4.75(brs,2H), 3.85(s, 3H), 2.20(s,3H)

c) Methyl(5-acetamido-[2H]-3,4-dihydro-1-benzopyran)-8-carboxylate

A solution of methyl (5-acetamido-[2H]-1-benzopyran)-8-carboxylate (D23) (770 mg) in ethanol, was hydrogenated over 10% palladium on charcoal at atmospheric pressure for 1.25 hours. The reaction mixture was filtered and the filtrate evaporated under reduced pressure to give the title compound as a white powder (670 mg, 86%)

$^1$H NMR 250 MHz (CDCl$_3$) δ:7.68(d,1H), 7.49(brs, 1H), 7.19(brs,1H), 4.22(t,2H), 3.88(s,3H), 2.62(t,2H), 2.20(s, 3H), 2.1–1.96(m,2H)

d) Methyl(5-acetamido-6-chloro-[2H]-3,4-dihydro-1-benzopyran-8-carboxylate

Following the procedure outlined in Description 3, methyl (5-acetamido-[2H]-3,4-dihydro-1-benzopyran)-8-carboxylate (660 mg) was converted to the title compound which was isolated as a light tan powder (525 mg, 70%)

$^1$H NMR 250 MHz (CDCl$_3$) δ:7.7(s,1H), 7.15(s,1H), 4.29(t,2H), 3.89(s,3H), 2.70(t,2H), 2.25(s,3H), 2.05–1.9(m, 2H)

e) 5-Amino-6-chloro-[2H]-3,4-dihydro-1-benzopyran-8-carboxylic acid

A solution of methyl (5-acetamido-6-chloro-[2H]-3,4-dihydro-1-benzopyran-8-carboxylate (1.015 g) in ethanol (20 ml) water (10 ml) and 10% sodium hydroxide (30 ml) was heated under reflux for 24 hours, then cooled and treated with concentrated hydrochloric acid (until pH 2) and the resulting precipitate was filtered off to give the title compound (D4) (427 mg, 52%)

$^1$H NMR 250 MHz (CDCl$_3$) δ:7.85(s,1H), 4.34(t,2H), 2.54(t,2H), 2.25–2.0(m,2H)

Description 5 (intermediate for Example 9)
6-Chloro-2,2-dimethyl-[2H]-3,4-dihydro-l-benzopyran-8-carboxylic acid Following the procedure outlined in Description 3, 2,2-dimethyl-[2H]-3,4-dihydro-l-benzopyran-8-carboxylic acid (EP-A-307172) (2.41 g) gave the title compound (D5) (2.68 g). M$^+$240 (E1)

Description 6 (intermediate for Example 10)
a) Methylthiochroman-4-one-8-carboxylate β-(2-carbomethoxythiophenoxy) propionic acid (6.00 g, 0.025 mol) (I. W. Still and M. J. Thomas J.Org. Chem 1968, 2733) was added slowly to ice cooled conc. sulphuric acid (75 ml) with stirring. After 21 h, the reaction mixture was poured into ice water and then made alkaline using solid sodium hydrogen carbonate. The resultant suspension was then extracted with CH$_2$Cl$_2$(3x). The combined organic layers were then dried (Na$_2$SO$_4$), and evaporated under reduced pressure to give an orange oil which was dried in vacuo and crystallised on standing to give (2.40 g, 43%).

b) Methylthiochroman-4-ol-8-carboxylate

Methylthiochroman-4-one-8-carboxylate (0.500 g, 2.25 mmol) was dissolved with stirring in ethanol (20 ml). After 1 h, the reaction mixture was evaporated under reduced pressure and the residue partitioned between ethyl acetate and water. The aqueous layer was then extracted with ethyl acetate (1x) and the combined organic layers were dried (Na$_2$SO$_4$) and evaporated under reduced pressure to give a yellow oil, which was purified by silica-gel chromatography (1:1 Pentane:EtOAc as eluant) to give the title compound as a colourless oil (0.499 g, 99%)

$^1$H NMR (200 MHz, CDCl$_3$) δ:7.95 (dd, 1H), 7.55 (dd, 1H), 7.12 (t, 1H), 4.87 (m, 1H), 3.92 (s, 3H) 3.23 (m,1H), 2.88 (m,1H), 2.37 (m,1H), 2.08 (m, 1H), 1.92 (d,1H).

c) Methyl-2H-thiochromene-8-carboxylate

Methyl thiochroman-4-ol-8-carboxylate (0.337 g, 1.50 mmol) was dissolved in toluene (25 ml) and was treated with p-toluenesulphonic acid (0.028 g, 0.15 mmol). The mixture was then heated to reflux with stirring. After 2 h, the reaction mixture was allowed to cool and was washed with sodium hydrogen carbonate solution. The aqueous layer was then extracted with EtOAc (1x), and the combined organic layers were dried (Na$_2$SO$_4$) and evaporated under reduced pressure to give a pale yellow oil which was purified by silica-gel chromatography (pentane: Et$_2$O 2:1 as eluant) to give the title compound (D2b) as a pale yellow oil (0.270 g, 87%)

$^1$H NMR (200 MHz, CDCl$_3$, δ:7.80 (dd, 1H), 7.20 (dd, 1H), 7.10 (t, 1H), 6.52 (d,1H), 6.02 (m,1H), 3.92 (s, 3H), 3.48 (dd,1H).

d) Methylthiochroman-8-carboxylate

Methyl-2H-thiochromene-8-carboxylate (1.83 g, 8.88 mmol) was dissolved in ethanol (100 ml) and treated with 10% PdC (1.5 g). The mixture was then hydrogenated at atmospheric pressure at room temperature. After 19 h the reaction mixture was filtered through celite and evaporated under reduced pressure to give a colourless oil which was dried in vacuo to give the title compound (1.25 g, 68%)

$^1$H NMR (200 MHz, CDCl$_3$), δ7.80 (d,1H), 7.62 (d,1H), 6.97 (t,1H), 3.89 (s, 3H), 2.97 (t, 2H), 2.87 (t, 2H), 2.12 (m, 2H).

e) Thiochroman-8-carboxylic acid

Methylthiochroman-8-carboxylate (0.220 g, 1.05 mmol) was dissolved in ethanol (5 ml) and treated with 10% sodium hydroxide solution (10 ml). The mixture was then heated to reflux with stirring. After 5 h, the reaction mixture was allowed to cool. The ethanol present was then removed by evaporation under reduced pressure. The aqueous residue was then washed with CH$_2$Cl$_2$ (2×) before being acidified to pH1 using 5M HCl. The resultant pale yellow precipitate was then filtered off and dried in vacuo to give the title compound (0.156 g, 76%) (D6).

$^1$H NMR (200 MHz, CD$_3$OD) δ:7.80 (d,1H), 7.20 (d,1H), 7.00 (t,1H), 2.90 (m, 4H), 2.08 (m, 2H).

Description 7 (intermediate for Example 11)

a) Methyl-6-bromothiochroman-8-carboxylate

A solution of methylthiochroman-8 carboxylate (0.300 g, 1.44 mmol) (D6a) in dichloromethane (20 ml) was treated with bromine (0.106 ml, 2.07 mmol) and the reaction mixture left at room temperature. After 4 days the reaction mixture was washed with sodium metabisulphile solution. The organic layer was then dried (Na$_2$SO4) and evaporated under reduced pressure to give the title compound as a colourless oil (0.340 g, 82%).

$^1$H NMR (250 MHz, CDCl$_3$) δ:7.92 (d, 1H), 7.30 (d, 1H), 3.92 (s, 3H), 3.00 (t, 2H), 2.88 (t, 2H), 2.10 (m, 2H).

b) 6-Bromothiochroman-8-carboxylic acid

This was prepared according to the general method described in Description 6e). Thus, methyl-6-bromo-thiochroman (0.325 g, 1.13 mmol) was converted to the title compound (0.306 g, 99%) (D7).

$^1$H NMR (200 MHz, CD$_3$SOCD$_3$): 13.25 (brs, 1H), 7.82 (d, 1H), 7.50 (d, 1H), 2.92 (m, 4H), 2.00 (m, 2H).

5-HT$_4$ RECEPTOR ANTAGONIST ACTIVITY

1) Guinea pig colon

Male guinea-pigs, weighing 250–400g are used. Longitudinal muscle-myenteric plexus preparations, approximately 3 cm long, are obtained from the distal colon region. These are suspended under a 0.5 g load in isolated tissue baths containing Krebs solution bubbled with 5%, CO$_2$ in O$_2$ and maintained at 37° C. In all experiments, the Krebs solution also contains methiothepin 10$^{-7}$M and granisetron 10$^{-6}$M to block effects at 5-HT$_1$, 5-HT$_2$ and 5-HT$_3$ receptors.

After construction of a simple concentration-response curve with 5-HT, using 30 s contact times and a 15 min dosing cycle, a concentration of 5-HT is selected so as to obtain a contraction of the muscle approximately 40–70% maximum(10$^{-9}$M approx). The tissue is then alternately dosed every 15 min with this concentration of 5-HT and then with an approximately equi-effective concentration of the nicotine receptor stimulant, dimethylphenylpiperazinium (DMPP). After obtaining consistent responses to both 5-HT and DMPP, increasing concentrations of a putative 5-HT$_4$ receptor antagonist are then added to the bathing solution. The effects of this compound are then determined as a percentage reduction of the contractions evoked by 5-HT or by DMPP. From this data, pIC$_{50}$ values are determined, being defined as the −log concentration of antagonist which reduces the contraction by 50%. A compound which reduces the response to 5-HT but not to DMPP is believed to act as a 5-HT$_4$ receptor antagonist.

Compounds were generally active in the range of concentrations of the order of pIC50=7 or more, E3, E8 and E12 showing particularly good activity.

2) Piglet Atria

Compounds were tested in the piglet spontaneous beating screen (Naunyn-Schmiedeberg's Arch. Pharmacol 342, 619–622). pK$_B$ (−log$_{10}$ K$_B$) value for the compound of Examples 3 and 7 were 9.8 and 7.7 respectively.

3) Rat oesophagus

Rat oesophageal tunica muscularis mucosae is set up according to Baxter et. al. Naunyn-Schmiedeberg's Arch. Pharmacol., 343, 439–446 (1991). The inner smooth muscle tube of the muscularis mucosae is isolated and mounted for isometric tension recording in oxygenated (95% O$_2$/5% CO2) Tyrodes solution at 37° C. All experiments are performed in pargyline pre-treated preparations (100 μM for 15 min followed by washout) and in the presence of cocaine (30 μM). Relaxant responses to 5-HT are obtained after pre-contracting the oesophagus tissue with carbachol (3 μM).

4) 5-HT-induced motility in dog gastric pouch

Compounds are tested in the in vivo method described in "Stimulation of canine motility by BRL 24924, a new gastric prokinetic agent", Bermudez et al, J. Gastrointestinal Motility, 2(4), 281–286.

The compound E3 showed inhibition at a dose of 10 μg kg$^{-1}$.

We claim:

1. A compound of formula (I), or a pharmaceutically acceptable salt thereof

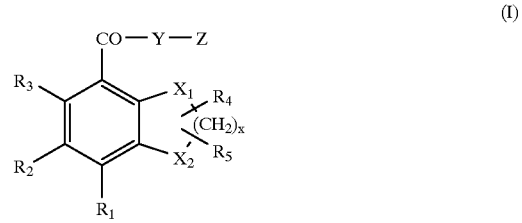

(I)

in which X$_1$—(CH$_2$)$_x$—X$_2$ and the aromatic carbon atoms to which they are attached form a 5–7 membered ring, wherein:

one of X$_1$ and X$_2$ is O or S, and the other is CH$_2$;

x is 1, 2 or 3;

R$_1$ is hydrogen, amino, halo, C$_{1-6}$ alkyl, hydroxy or C$_{1-6}$ alkoxy;

R$_2$ is hydrogen, halo, C$_{1-6}$ alkyl, C$_{1-6}$ alkoxy, nitro, amino or C$_{1-6}$ alkylthio;

R$_3$ is hydrogen, halo, C$_{1-6}$ alkyl, C$_{1-6}$ alkoxy or amino;

R$_4$ and R$_5$ are independently hydrogen or C$_{1-6}$ alkyl;

Y is O or NH;

Z is of sub-formula (a):

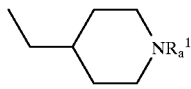

wherein $R_a^1$ is $C_{1-12}$ alkyl or benzyl, unsubstituted or substituted by one or more substituents selected from halogen, $C_{1-6}$ alkyl and $C_{1-6}$ alkoxy.

2. A compound according to claim 1 wherein $R_1$ is hydrogen or amino.

3. A compound according to claim 1 wherein $R_2$ is hydrogen or halo.

4. A compound according to claim 1 wherein $R_3$ is hydrogen or halo.

5. A compound according to claim 1 wherein $X_1$—$(CH_2)_x$—$X_2$ is O—$(CH_2)_2$—$CH_2$, O—$(CH_2)_3$—$CH_2$, O—$CH_2$—$CH_2$, or corresponding values wherein $X_1=X_2=CH_2$, wherein any of the methylene linkages are optionally mono- or di-substituted by $C_{1-6}$ alkyl groups, such as methyl.

6. A compound according to claim 1 wherein Y is O or NH.

7. A compound according to claim 1 wherein the N-substituent is $C_2$ or greater alkyl, benzyl or benzyl substituted by one or more substituents selected from halogen, $C_{1-6}$alkyl and $C_{1-6}$alkoxy.

8. A pharmaceutical composition comprising a compound according to claim 1, and a pharmaceutically acceptable carrier.

9. A method of treating irritable bowel syndrome comprising administering a compound according to claim 1.

10. A method of treating urinary incontinence comprising admininstering a compound according to claim 1.

11. A method of treating atrial arrhythmia or stroke comprising administering a compound according to claim 1.

* * * * *